United States Patent
Peschel et al.

(10) Patent No.: US 10,730,810 B2
(45) Date of Patent: Aug. 4, 2020

(54) PROCESS AND PLANT FOR PRODUCING AN OLEFIN

(71) Applicant: LINDE AKTIENGESELLSCHAFT, München (DE)

(72) Inventors: Andreas Peschel, Wolfratshausen (DE); Andreas Obermeier, Egmating (DE); Helmut Fritz, München (DE); Mathieu Zellhuber, Martinsried (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/472,435

(22) PCT Filed: Dec. 22, 2017

(86) PCT No.: PCT/EP2017/084502
§ 371 (c)(1),
(2) Date: Jun. 21, 2019

(87) PCT Pub. No.: WO2018/115494
PCT Pub. Date: Jun. 28, 2018

(65) Prior Publication Data
US 2019/0359545 A1 Nov. 28, 2019

(30) Foreign Application Priority Data
Dec. 22, 2016 (EP) .................................... 16206476

(51) Int. Cl.
*C07C 5/48* (2006.01)
*C07C 7/04* (2006.01)

(52) U.S. Cl.
CPC . *C07C 5/48* (2013.01); *C07C 7/04* (2013.01)

(58) Field of Classification Search
CPC .. C07C 5/48; C07C 11/04; C07C 7/04; C07C 7/167; C07C 2523/22; C07C 2523/28; C07C 2523/648; C07C 2523/652; C07C 2523/656; C07C 2527/057; C07C 51/16; C07C 67/04; B01D 2252/103; B01D 53/1406; B01D 53/1456; B01D 53/1493; B01D 53/18; B01J 12/00; B01J 19/0046; B01J 19/242; B01J 19/245; B01J 19/2475; B01J 2219/24; B01J 23/002; B01J 23/28; B01J 23/755; B01J 23/847; B01J 27/0576; B01J 35/065; B01J 35/1009; B01J 35/1014

See application file for complete search history.

(56) References Cited

FOREIGN PATENT DOCUMENTS

| DE | 102012020470 A1 | 4/2014 |
|---|---|---|
| EP | 3029402 A1 | 6/2016 |

OTHER PUBLICATIONS

PCT/EP2017/084502 International Search Report and Written Opinion dated Apr. 11, 2018, 9 pages.
PCT/EP2017/084502 International Preliminary Report on Patentability dated Jun. 25, 2019, 19 pages.

*Primary Examiner* — Sharon Pregler
(74) *Attorney, Agent, or Firm* — Lathrop GPM LLP

(57) ABSTRACT

A process for producing an olefin having N carbon atoms is proposed in which using a dehydrogenation a process gas is formed which contains at least the olefin having N carbon atoms, a paraffin having N carbon atoms and a hydrocarbon having N−1 carbon atoms and in which using at least a portion of the process gas a separation input is formed which is subjected to a low temperature separation in which the separation input is cooled stepwise over a plurality of temperature levels and condensates are separated from the separation input, wherein the condensates are at least partly subjected to a first low temperature rectification to obtain a first gas fraction and a first liquid fraction, wherein the first gas fraction contains at least the olefin having N carbon atoms in a lower proportion than in the condensates and the hydrocarbon having N−1 in a higher proportion than in the condensates. It is provided that the first gas fraction is at least partly subjected to a second low temperature rectification using a liquid reflux containing predominantly or exclusively the hydrocarbon having N−1 carbon atoms in which the first gas fraction undergoes depletion in the olefin having N carbon atoms. A corresponding plant (100) likewise forms part of the subject matter of the invention.

20 Claims, 3 Drawing Sheets

PROCESS AND PLANT FOR PRODUCING AN OLEFIN

The invention relates to a process for producing an olefin and a corresponding plant according to the preambles of the independent claims.

PRIOR ART

Oxidative dehydrogenation (ODH) of paraffins having two to four carbon atoms is known in principle. In ODH the recited paraffins are reacted with oxygen to afford inter alia olefins of identical carbon number and water.

ODH may be advantageous compared to established processes for producing olefins such as steamcracking or catalytic dehydrogenation. For instance, there is no thermodynamic equilibrium limitation on account of the exothermicity of the reactions involved. The formation energies $\Delta G$ for ethane, propane and n-butane are −102, −115 and −118 kJ/mol respectively. ODH may be performed at comparatively low reaction temperatures. Regeneration of the employed catalysts is in principle not necessary since the presence of oxygen allows an in situ regeneration. Finally, compared to steamcracking, smaller amounts of worthless byproducts such as coke are formed.

For further details concerning ODH, reference is made to the relevant technical literature, for example Ivars, F. and López Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767 to 834, or Gartner, C. A. et al., Oxidative Dehydrogenation of Ethane: Common Principles and Mechanistic Aspects, ChemCatChem, vol. 5, no. 11, 2013, pages 3196 to 3217.

The invention is hereinbelow described in particular having regard to ODH of ethane (so-called ODH-E). However, the use of said invention is in principle possible and advantageous also for ODH of higher paraffins such as propane and butane. In addition to the oxidative dehydrogenation of methane a non-oxidative dehydrogenation of ethane for producing ethylene may in principle also be effected. The present invention is suitable for such a process too.

To ensure sustainable activity of the catalysts in ODH a minimum content of oxygen at the reactor outlet is required to avoid reduction of the catalyst and thus a loss in performance thereof. It is therefore generally not possible to operate with a complete oxygen conversion in the reactor. Furthermore, at higher conversions appreciable amounts of carbon monoxide and carbon dioxide and possibly carboxylic acids are formed as byproducts. Methane may likewise be formed as a byproduct or already be present in the input into the reactor and traverse the reactor essentially unaffected as a component exhibiting inert behavior. The recited components in a corresponding process gas, i.e. the gas mixture from the reactor, must be removed in downstream separating steps.

As is also elucidated hereinbelow, particularly due to the low contents of methane in an ODH-E process gas it is not readily possible to employ known separating processes and separating devices used for separation of process gases from steamcrackers for example without accepting product and possibly reactant losses. This applies in particular to a separating step in which methane and lower boiling components are removed from higher boiling components, i.e. a so-called demethanization or a corresponding demethanizer. As is likewise elucidated hereinbelow such a separation can also result in carbon monoxide and oxygen in particular undergoing enrichment beyond undesirable and dangerous concentrations. The same also applies to process gases from other dehydrogenations and ODH of higher paraffins such as propane and butane which likewise contain only a relatively small proportion of compounds lower boiling than the respectively employed reactants and the products formed.

The problem addressed by the present invention is accordingly that of improving corresponding processes and plants and addressing the recited problems in a corresponding separation, in particular for a process gas from ODH and more particularly a process gas from ODH-E.

Disclosure of the Invention

Against this background, the present invention proposes a process for producing an olefin and a corresponding plant having the features of the independent claims.

Embodiments are in each case subject matter of the dependent claims and of the description which follows.

Material streams, gas mixtures etc. may in the context of the present usage be rich or poor in one or more components, wherein the indication "rich" may represent a content of no less than 99%, 99.5%, 99.9% or 99.99% and the indication "poor" may represent a content of no more than 1%, 0.5%, 0.1% or 0.01% on a molar, weight or volume basis. If a plurality of components are reported the indication "rich" or "poor" relates to the sum of all components. If reference is made for example to "oxygen" or "methane" a pure gas or else a gas mixture rich in the respective component may be concerned. A gas mixture containing "predominantly" one or more components is in particular rich in this or these components in the elucidated sense.

Material streams, gas mixtures etc. may in the context of the present usage also be "enriched" or "depleted" in one or more components, wherein these terms are based on a content in a starting mixture. They are "enriched" when they contain not less than 1.5 times, 2 times, 5 times, 10 times, 100 times or 1000 times the content, and "depleted" when they contain not more than 0.75 times, 0.5 times, 0.1 times, 0.01 times or 0.001 times the content, of one or more components based on the starting mixture.

The terms "pressure level" and "temperature level" are used hereinbelow to characterize pressures and temperatures, these being intended to express that pressures and temperatures need not be present in the form of exact pressure/temperature values. A pressure level or temperature level may for example be within ±1%, 5%, 10%, 20% or 50% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "rectification column" is in the context of the present usage a separating unit adapted for at least partly fractionating a substance mixture introduced in gaseous or liquid form or in the form of a biphasic mixture having liquid and gaseous proportions, optionally also in the supercritical state, by rectification, i.e. respectively generating from the substance mixture pure substances or at least substance mixtures having different compositions. Rectification columns are typically configured as cylindrical metal containers provided with internals, for example separating trays or ordered or unordered packings. A rectification column comprises a bottoms evaporator. This is a device having a heat exchanger which is heated and adapted for heating a liquid fraction accumulating in the bottom of the rectification column, also known as bottoms liquid. By means of a bottoms evaporator a portion of the bottoms liquid is continuously evaporated and recycled in gaseous form into the rectification column.

The present invention relates to separating processes and corresponding separating devices similar in terms of the underlying concept, but not the implementation realized according to the invention, to separating processes and separating devices known for other process gases, for example process gases from steamcrackers. These are described in the specialist literature, for example in the article "Ethylene" in Ullmann's Encyclopedia of Industrial Chemistry, Online Edition, 15 Apr. 2007, DOI 10.1002/14356007.a10_045.pub2. An essential step in such separating processes is often so-called demethanization in which from the process gas, optionally after removal of further components, methane and compounds lower boiling than methane are removed from higher boiling components. For details of known demethanization processes reference is made to the cited specialist literature.

Advantages of the Invention

As recited at the outset a typical process gas formed by ODH contains not only primary products such as olefins (and typically carboxylic acids) but also inter alia unconverted paraffins, methane, oxygen, carbon monoxide and carbon dioxide. The process gas typically also contains water and possibly small amounts of inert gases, wherein "inert gases" is to be understood as meaning generally gases which react only in small proportions, if at all, in ODH and not only classical inert gases such as nitrogen or noble gases. Methane too exhibits essentially inert behavior in ODH-E for example.

The same applies in similar fashion to process gases from other processes for producing olefins, for example dehydration of ethane, wherein hereinbelow, as repeatedly mentioned, for the sake of simplicity reference is made to ODH and in particular ODH-E. The recited components must be removed in a separation downstream of the ODH.

Separation is typically effected, as also illustrated with reference to the accompanying FIG. 1, after a compression of the process gas. Said process gas is then typically freed by means of a water quench at least of large parts of any carboxylic acids present and of the water present. This is followed by scrubbing steps for removing carbon dioxide.

The process gas now still containing essentially olefins, the unconverted paraffins, oxygen, carbon monoxide and also smaller amounts of inert gases is freed of residual water and precooled. A stepwise condensation of the process gas is then effected in a subsequent low temperature separation. The remaining gas fractions are in each case supplied to the next condensation step. The condensates are separated in a low temperature rectification, wherein in turn a gas fraction and a liquid fraction are formed. The gas fraction from the low temperature rectification is typically combined with the gas fraction remaining downstream of the last condensation step to afford a further gas fraction, the so-called fuel gas fraction/tail gas fraction, and typically after a heat-integrated use sent for thermal utilization. The liquid fraction from the low temperature rectification is subjected to further separating steps.

The fuel gas fraction shall contain at least the predominant part of the carbon monoxide and oxygen present in the process gas supplied to the low temperature separation and of the remaining components lower boiling than the desired olefins. The desired olefins shall be transferred at least predominantly into the liquid fraction from the low temperature rectification together with the higher boiling unconverted paraffins.

The separation efficiency in the low temperature rectification depends essentially on the content of light components in the process gas supplied to the low temperature rectification because a liquid reflux formed essentially from corresponding light components is used here. In the case of ODH-E this is methane. If contents of corresponding light components are excessively low the reflux cannot be provided in a sufficient amount. Thus, excessively small amounts of light compounds result in considerable losses of product of value, in particular of the desired olefins, ethylene in the case of ODH-E, but also possibly of unconverted reactants, ethane in the case of ODH-E. These are transferred into the tail gas fraction, thus giving rise to economic disadvantages compared to other processes.

Furthermore, the respectively formed undergo increasing enrichment in oxygen and carbon monoxide in the low temperature separation. In such gas mixtures both the explosion limit and the oxygen threshold concentration (see below) may be markedly exceeded. Generally, even an oxygen content of 3000 vppm in a typical process gas from an ODH-E reactor outlet, i.e. in the process gas directly downstream of the reactor(s) used for the ODH-E, can result in a gas mixture formed in the low temperature rectification having carbon monoxide and oxygen contents of 66 vol % and 13 vol % respectively.

The (lower) explosion threshold of a gas indicates the content in a gas mixture above which ignition/explosion is possible at simultaneously sufficient oxygen content. For carbon monoxide said threshold is at a content of markedly over 10 mol percent and is influenced inter alia by the content of hydrogen and water in the gas mixture considered in each case. Under standard conditions said threshold is reported as 12.5 mol percent. In the elucidated gas fractions formed in a typical low temperature separation downstream of an ODH-E the content of carbon monoxide is at least 40 and up to 70 mol percent, as also elucidated with reference to accompanying FIG. 2 and just recited, and the explosion threshold has therefore been markedly exceeded.

When the explosion threshold has been exceeded an explosion may take place provided that the so-called oxygen threshold concentration has also been exceeded. This indicates the oxygen content above which an explosion can occur. In other words for an explosion to be possible both the explosion threshold and the oxygen threshold concentration must have been exceeded.

The oxygen threshold concentration for carbon monoxide is extremely low and is approximately half of that of methane and approximately equal to that of ethylene. In mixtures of different flammable gas components intermediate values are typically established. In the present case, i.e. the gas mixtures formed in the low temperature separation, the oxygen threshold concentration is at a value of about 6 mol percent provided that no further measures are adopted. Explosions and possibly even detonations can therefore occur in principle.

The present invention solves these problems in a process for producing an olefin having N carbon atoms in which using a dehydrogenation a process gas is formed which contains at least the olefin having N carbon atoms, a paraffin having N carbon atoms and a hydrocarbon having N−1 carbon atoms and in particular carbon monoxide and oxygen and in which using at least a portion of the process gas a separation input is formed which is subjected to a first low temperature separation in which the separation input is cooled stepwise over a plurality of temperature levels and condensates are separated from the separation input, wherein the condensates are at least partly subjected to a first low temperature rectification to obtain a first gas fraction and a first liquid fraction, wherein the first gas fraction contains at least the olefin having N carbon atoms in a lower proportion than in the condensates and the hydrocarbon having N−1 in a higher proportion than in the condensates.

According to the invention it is provided that the first gas fraction is at least partly subjected to a second low temperature rectification using a liquid reflux containing predominantly or exclusively the hydrocarbon having N−1 carbon atoms in which the first gas fraction undergoes depletion in the olefin having N carbon atoms. In the context of the present invention it is thus provided in addition to the use of a ("first") low temperature rectification typically used in a corresponding low temperature separation to employ a further ("second") low temperature rectification in which the products of value and possibly reactants transferred into the tops fraction of the first low temperature rectification, i.e. the "first gas fraction", can be recovered. This can be achieved by means of a relatively small rectification column, so that the additional apparatus cost and complexity is limited and can be more than compensated by the markedly lower product losses.

The second low temperature rectification is performed using an externally provided liquid reflux and separation performance is therefore independent of the light components present in the process gas. The provision of a corresponding liquid reflux may be accomplished in simple and cost-effective fashion due to the presence of the media respectively required in a corresponding plant.

A proportion of the separation input which remains gaseous in the stepwise cooling, i.e. a relatively light fraction not separated in the form of the condensates, may likewise be at least partly subjected to the second low temperature rectification. In this way olefins having N carbon atoms present in this proportion may also be obtained as product.

It is advantageous when in the second low temperature rectification a second gas fraction poor in or free from the olefin having N carbon atoms and a second liquid fraction containing the olefin having N carbon atoms in a higher proportion than in the first gas fraction are formed. The second liquid fraction may in particular be recycled into the first low temperature rectification, so that the olefin having N carbon atoms present therein may finally be transferred into the first liquid fraction and thus into a product fraction.

The liquid reflux may be provided already in the liquid state, i.e. as a liquefied gas. For example in ODH-E, in which N is two, i.e. the reflux containing predominantly or exclusively the hydrocarbon having N−1 carbon atoms contains predominantly or exclusively methane, recourse may be made to liquefied natural gas. The same is possible for other values of N too, for example the use of liquid ethane, propane, butane etc. which may be provided in tanks for example.

It is particularly advantageous when the liquid reflux is formed using a liquid fraction formed by partial condensation of a gas containing predominantly or exclusively the hydrocarbon having N−1 carbon atoms. The partial condensation may comprise in particular a cooling of a corresponding pressurized gas and subsequent decompression thereof.

A proportion which remains gaseous in the partial condensation of the gas containing predominantly or exclusively the hydrocarbon having N−1 carbon atoms may be at least partly introduced into the low temperature separation. This proportion is for example introduced into the first low temperature rectification and/or at least partly added to the separation input after separation of at least one of the condensates from the separation input. In this way through a corresponding dilution a reduction of the oxygen content in corresponding regions/fractions may be achieved, thus resulting in a double benefit of the measures proposed according to this embodiment. The introduction may in principle be effected at any location at which a reduction of the oxygen content is useful for safety reasons, in particular into separators in which the recited condensates are separated, into a rectification column employed in the first low temperature rectification or into the respective conduits. The introduction is in particular effected in an amount which reduces the oxygen content to a value of below 6 mol percent or 5 mol percent.

The liquefied gas or the liquefied fraction—in addition to the use as liquid reflux—may be partly used correspondingly. The introduction options are the same as elucidated for the gaseous proportion. The liquid introduction too can in principle bring about a dilution. However, introduction of the liquefied gas in the liquid state can additionally especially save energy or heat exchanger area required for cooling.

As recited the process according to the invention may be employed in particular for oxidative or non-oxidative dehydrogenation of ethane, i.e. in processes in which N is two, so that the olefin having N carbon atoms is ethylene, the paraffin having N carbon atoms is ethane and the hydrocarbon having N−1 carbon atoms is methane. In particular the process is suitable for an oxidative dehydrogenation, i.e. in particular for an ODH-E. In other cases N may also be three or four.

In cases in which N is two the temperature levels to which the separation input is cooled stepwise advantageously comprise a first temperature level of −20° C. to −40° C. and/or a second temperature level of −40° C. to −60° C. and/or a third temperature level of −70° C. to −80° C. and/or a fourth temperature level of −95° C. to −105° C. Such temperature levels may be achieved with known refrigerant circuits, for example propylene refrigerant circuits and ethylene refrigerant circuits at different pressures. The first low temperature rectification advantageously comprises a condensation of tops gas to a temperature level of −90° C. to −100° C.

In cases in which N is two, i.e. the liquid reflux contains predominantly or exclusively methane, said reflux is advantageously provided in the form of liquefied natural gas or formed using at least a portion of a liquid fraction provided by cooling a predominantly or exclusively methane-containing gas at a pressure level of 30 to 70 bar to a temperature level of −70° C. to −100° C. and decompressing to a pressure level of 10 to 20 bar. In this way any available methane sources such as for example pipeline methane at correspondingly high pressure levels may be utilized without further compression being necessary.

As recited, in particular in the second low temperature rectification the process may use comparatively small and cost-effective rectification columns, for example those having 1 to 10 theoretical or practical plates.

As recited the process gas in particular also contains oxygen and carbon monoxide and the dilution options for explosion and detonation protection likewise possible according to the invention are therefore particularly advantageous.

The present invention also extends to a plant for producing an olefin having N carbon atoms, comprising at least one reactor unit adapted for using a dehydrogenation to form a process gas which contains at least the olefin having N carbon atoms, a paraffin having N carbon atoms and a hydrocarbon having N−1 carbon atoms and comprising means adapted for using at least a portion of the process gas to form a separation input and subjecting said input to a first low temperature separation which is adapted for cooling the separation input stepwise over a plurality of temperature levels and separating condensates from the separation input and at least partly subjecting the condensates to a first low temperature rectification to obtain a first gas fraction and a first liquid fraction, wherein the first gas fraction contains at least the olefin having N carbon atoms in a lower proportion than in the condensates and the hydrocarbon having N−1 in a higher proportion than in the condensates.

According to the invention the plant comprises means adapted for at least partly subjecting the first gas fraction to a second low temperature rectification using a liquid reflux containing predominantly or exclusively the hydrocarbon having N−1 carbon atoms in which the first gas fraction undergoes depletion in the olefin having N carbon atoms.

For features and advantages of a corresponding plant, reference is made to the above elucidations concerning the features and advantages of the process. In particular such a plant is adapted for performing a process according to the specific embodiments elucidated above and comprises means suitable therefor. In this regard too reference is made to the above intimations.

The invention is more particularly elucidated below with reference to the appended drawings which illustrate inter alia preferred embodiments of the present invention.

DETAILED DESCRIPTION OF THE DRAWINGS

Figure 1:
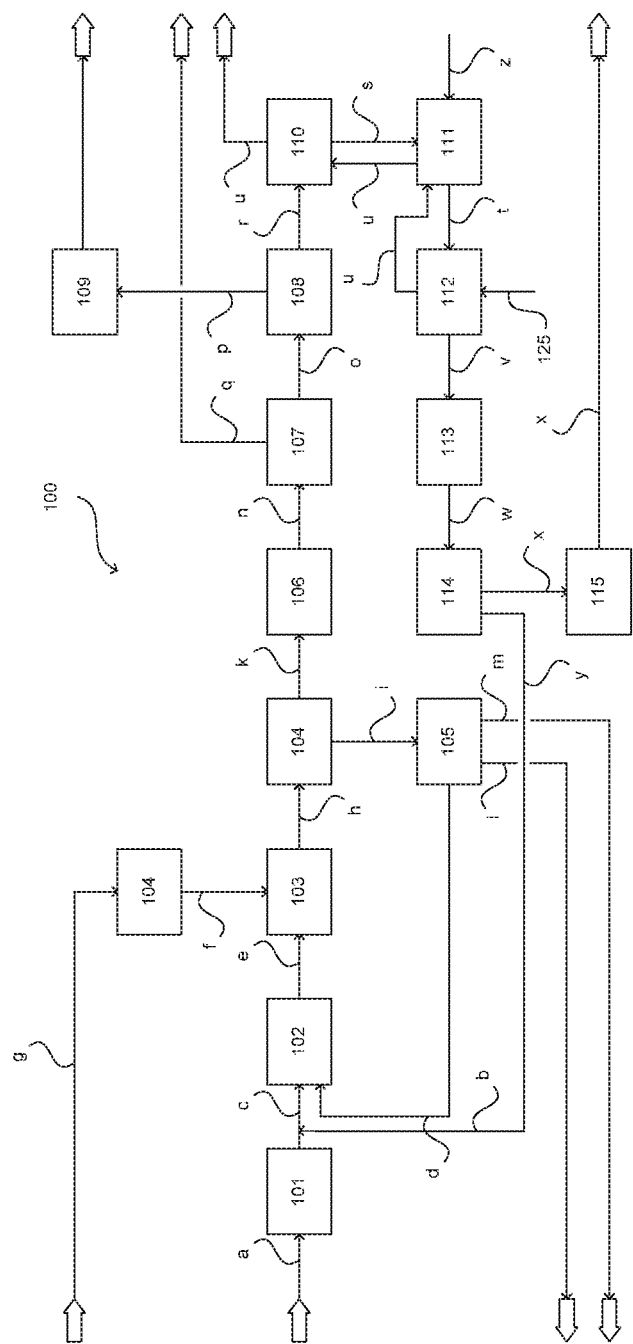
FIG. 1 illustrates a plant for producing olefins according to one embodiment of the invention.

In the figures that follow functionally or structurally equivalent elements are indicated with identical reference numerals and for the sake of simplicity are not repeatedly elucidated. When plant parts are described hereinbelow the elucidations concerning these also apply correspondingly to the process steps implemented by means of these plant parts and vice versa.

In FIG. 1 a plant for producing olefins according to one embodiment of the invention in the form of a greatly simplified plant diagram is illustrated and collectively referred to as 100. Notwithstanding that a plant 100 for ODH of ethane (ODH-E) is described below, the present invention is also suitable, as recited, for use in ODH of higher hydrocarbons or a nonoxidative dehydrogenation. In this case the elucidations which follow apply correspondingly.

In the plant 100 a separation input in the form of a material stream a is supplied to a rectification unit 101 having for example one or more rectification columns and subjected to a rectification. In the depicted example the separation input contains at least ethane and higher hydrocarbons, in particular corresponding higher paraffins. The rectification unit 101 may also be supplied with one or more further separation inputs.

In the rectification unit 101 the separation input is subjected to a rectification alone or together with the further separation input(s) to obtain a separation product which contains ethane but is poor in higher hydrocarbons. The separation product is withdrawn in the form of a material stream c and supplied to a preheating unit 102. In the preheating unit 102 the gas mixture is preheated, wherein in the depicted example the preheating unit 102 is also supplied with a water or steam stream d. Further material streams may also be supplied. A further material stream b elucidated below may be added to the material stream c.

A material stream e outflowing from the preheating unit 102 is supplied to a reaction unit 103 to form a reaction input. On account of its formation using the separated product from the rectification unit 101 the reaction input contains ethane but is poor in higher hydrocarbons. The reaction input may further contain one or more diluents such as water or inert gases and further components. These may also be supplied to the reaction unit 103 in the form of further material streams (not shown).

In the depicted example the reaction unit 103 is supplied with an oxygen-containing material stream f. This may be provided using an air separation plant 104. To this end the air separation plant 104 is supplied with an airstream g. The oxygen-containing material stream f may be substantially pure oxygen but fractions of nitrogen and of noble gases may also be present depending on the operation of the air separation plant 104. In this way it is likewise possible to supply diluent.

Outflowing from the reaction unit 103 is a process gas in the form of a process gas stream h which contains ethylene formed in the reaction unit 103 by ODH of a portion of the ethane in the reaction input. The product mixture further contains acetic acid likewise formed from ethane during ODH in the reaction unit 103, water, carbon monoxide, carbon dioxide, unconverted oxygen and the diluent(s) and further compounds if added or previously formed in the reaction unit 103.

It will be appreciated that reaction unit 103 may comprise a or else a plurality of reactors which are for example operated in parallel. In the latter case these reactors are each supplied with corresponding reaction inputs, which may have identical or different compositions, and corresponding oxygen-containing material streams f and in each case corresponding process gas streams h are formed. The latter may for example be combined and supplied together as process gas to the units elucidated below.

The process gas is transferred into a quench unit 104 in which, for example in a quench column, it may be contacted with quench water or a suitable aqueous solution. In the quench unit 104 the process gas is in particular cooled and the acetic acid formed in the reaction unit 103 is scrubbed out of the process gas. Acetic acid-laden process water outflows from the quench unit 104 in the form of a material stream i, the process gas at least largely freed of acetic acid outflows from the quench unit 104 in the form of a material stream k.

In an optional acetic acid recovery unit 105 acetic acid is separated off from the acetic acid-laden process water as glacial acetic acid which is discharged from the plant 100 as material stream l. Pure process water likewise recovered in the acetic acid recovery unit 105 may be supplied to the preheating unit 102 in the form of the previously elucidated material stream d. The process water supplied to the reactor may also be partly or completely provided in the form of externally supplied freshwater. Water that is no longer usable or required may be discharged from the plant 100 and supplied to a wastewater treatment in the form of a wastewater stream m.

The process gas present in the form of material stream k and at least largely freed of acetic acid is compressed to a suitable pressure level, for example 15 to 25 bar, in a compressing unit 106 and in the form of a compressed material stream n supplied to an amine scrub unit 107. Scrubbed out therein are in particular portions of the carbon dioxide present in the process gas. After regeneration of the amine the scrubbed-out carbon dioxide may be discharged from the plant in the form of a material stream q.

The process gas thus partly freed of carbon dioxide is transferred in the form of a material stream o into a lye scrub unit 108 and further purified of carbon dioxide therein. Generated in the lye scrub unit 108 is waste lye which in the form of a material stream p is transferred into a waste lye treatment unit 109 and finally discharged from the plant.

The process gas further purified in the lye scrub unit 108 is transferred in the form of a material stream r into a pre-cooling and drying unit 110 where it may be freed from residual water in particular. The dried process gas is transferred in the form of a material stream s into a low temperature unit 111 and subsequently in further-cooled form in the form of one or more material streams t into a demethanization unit 112. In the low temperature unit 111 and the demethanization unit 112 components lower boiling than ethylene, in particular carbon monoxide and oxygen, are separated off from the process gas, wherein the remainder stays in condensed form. If the process gas contains higher hydrocarbons formed as a byproduct during ODH in the reaction unit 103 these are likewise converted into condensate.

The separated-off components lower boiling than ethylene are recycled in the form of one or more material streams u through the low temperature unit 111 and the precooling and drying unit 110, therein optionally combined with further corresponding material streams, used for cooling purposes and discharged from the plant 100. If required the hydrocarbons having two and optionally more carbon atoms are supplied in the form of a material stream v to a hydrogenation unit 113 in which in particular acetylene likewise formed as byproduct during ODH in the reaction unit 103 may be hydrogenated. After the hydrogenation the material stream now referred to as w is transferred into an ethylene removal unit 114.

In the ethylene removal unit 114 ethylene is at least largely separated off from other components and in the form of a material stream x after utilization in an ethylene cooling unit 115 may be discharged from the plant 100 in gaseous form. The remaining components, predominately ethene and possibly higher hydrocarbons, are withdrawn in the form of a material stream y and in the form of the material stream b recycled into the pre-heating unit 102.

In the illustrated embodiment according to the invention a liquid methane-rich stream z may be introduced into the demethanization unit 112 as elucidated in detail hereinbelow.

Figure 2:
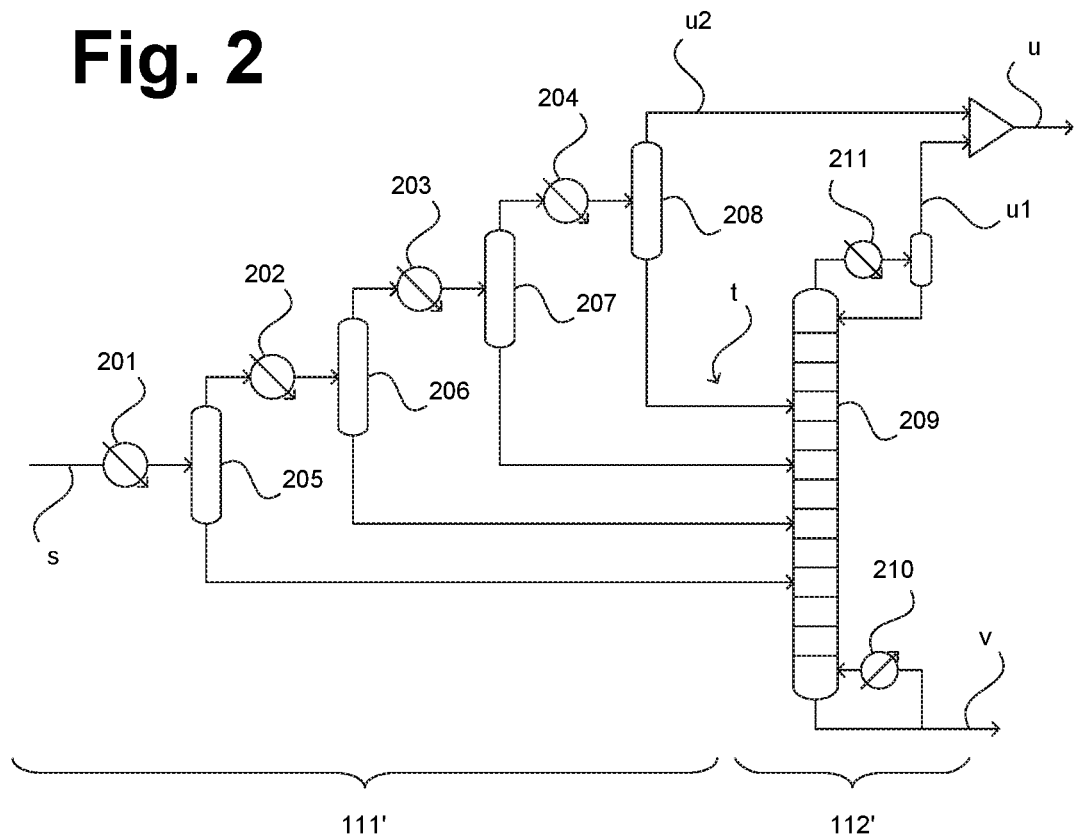
FIG. 2 illustrates a low temperature separation for use in a plant for producing olefins according to a noninventive variant.

FIG. 2 illustrates a low temperature separation for use in a plant for producing olefins according to a noninventive variant. This low temperature separation comprises the use of a low temperature unit and a demethanization unit which may be employed in a noninventive variant of a plant 100 as is shown in FIG. 1 and in which no methane introduction in the form of the methane-rich stream z is undertaken. The low temperature unit and a demethanization unit are therefore summarized here with 111' and 112'. The material streams s, t, u and v previously depicted in FIG. 1 are also shown here. The depiction of the respective elements is not true to position and not true to scale.

The process gas is supplied to the low temperature unit 111' in the form of the material stream s. The process gas is successively passed through heat exchangers 201 to 204 and therein cooled to ever lower temperature levels. To this end the heat exchangers 201 to 204 may be cooled with ethylene streams (not illustrated). For cooling, the material stream u (likewise not specifically illustrated) may additionally be employed which in the depicted example contains the components of the process gas lower boiling than ethane which are removed in the low temperature unit 111' and the demethanization unit 112'.

Downstream of the heat exchangers 201 to 204 the process gas/a biphasic mixture formed in each case by cooling in the heat exchangers 201 to 204 is in each case transferred into separators 205 to 208 where in each case a condensate is separated from the process gas. The condensates are introduced into a rectification column 209 of the demethanization unit 112, the so-called demethanizer, at a height corresponding to their composition of matter in the form of the material streams t. A smaller proportion of the process gas may also be introduced directly into the rectification column 209 (not illustrated).

A bottoms evaporator 210 of the rectification column 209 is heated using propane or propylene from a refrigeration circuit for example, a tops condenser 211 is cooled using low-pressure ethylene for example. The rectification column 209 is operated such that predominantly methane and lower boiling components undergo enrichment at its top and the higher boiling compounds undergo enrichment at its bottom. In this way a portion of the material stream u, referred to here as u1, may be withdrawn from the top of the rectification column 209 and the material stream v may be withdrawn from the bottom of the rectification column 7. A fraction of the process gas remaining in gaseous form in the separator 208, illustrated here in the form of a material stream u2, may likewise be used in the formation of the material stream u.

In a representative example for example about 67 t/h of the process gas in the form of material stream s are supplied to the low temperature unit 111' at a pressure of for example about 20 bar. The temperature downstream of the heat exchanger 201 is for example about −30° C., the temperature downstream of the heat exchanger 202 for example about −50° C., the temperature downstream of the heat exchanger 203 for example about −75° C. and the temperature downstream of the heat exchanger 204 for example about −99° C. The bottoms evaporator 210 is operated at a temperature level of for example about −17° C., the tops condenser 211 at a temperature level of for example about −97° C.

In this example the material stream u1 comprises a total mass flow of for example about 2 t/h, of which for example about 190 kg/h is ethylene and for example 13 mol % is oxygen. The material stream u2 comprises a total mass flow of for example about 1 t/h, of which for example about 40 kg/h is ethylene and for example 13 mol % is oxygen.

It is thus apparent that considerable amounts of ethylene product are lost in the form of the material streams u1 and u2, i.e. of the material stream u, which should actually be transferred into the material stream v. As recited, this is attributable in particular to the comparatively low methane contents in the process gas of the material stream s which under the reported conditions do not allow satisfactory separation in the rectification column 209. In addition, the high oxygen concentration, particularly in view of the carbon monoxide likewise present, is critical.

Figure 3:
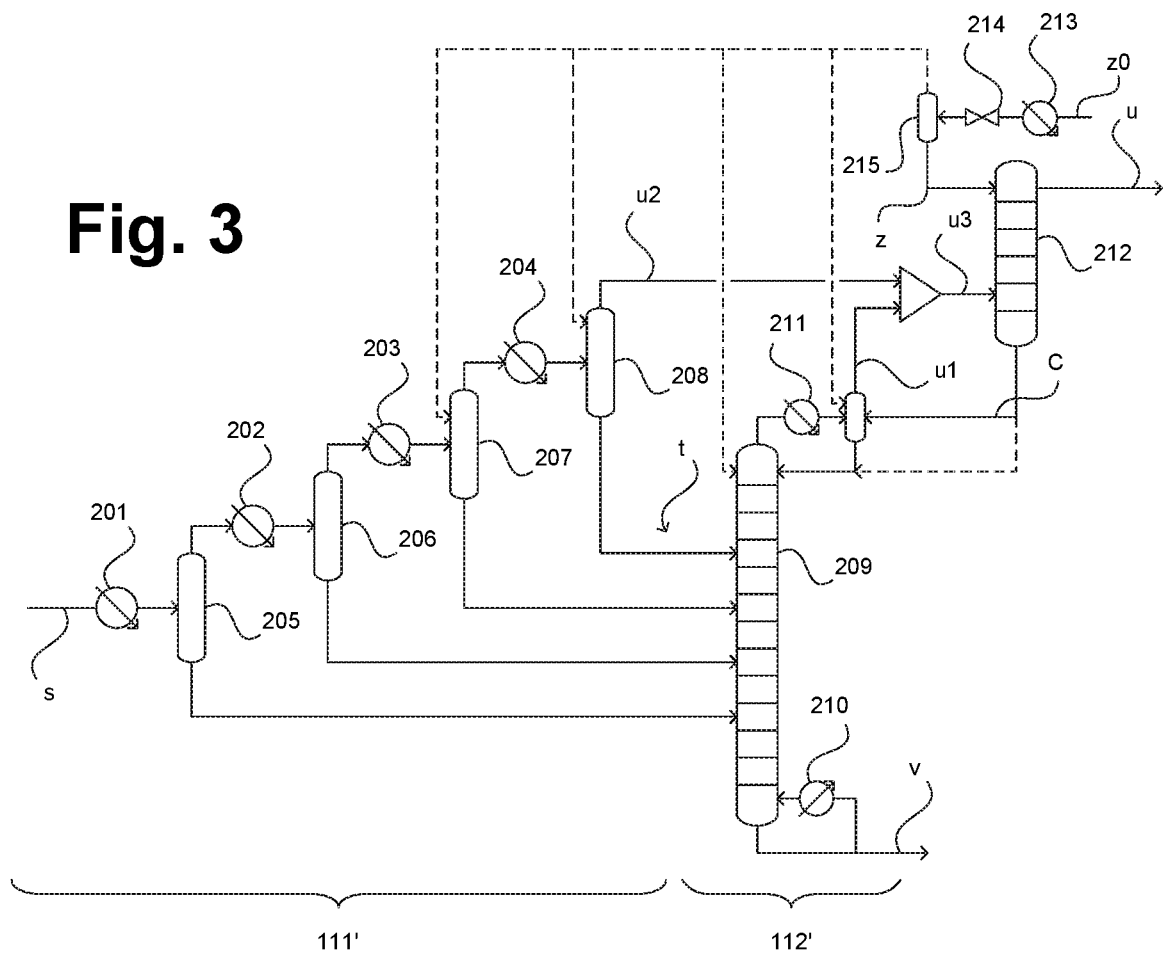
FIG. 3 illustrates a low temperature separation for use in a plant for producing olefins according to one embodiment of the invention.

FIG. 3 illustrates a low temperature separation for use in a plant for producing olefins according to one embodiment of the invention in which these problems have been remedied. This low temperature separation also comprises the use of a low temperature unit and a demethanization unit which may be employed for example in a plant 100 according to the invention as shown in FIG. 1. The low temperature unit and a demethanization unit are therefore summarized here with 111 and 112. The material streams s, t, u and v previously depicted in FIG. 1 are also shown here. The depiction of the respective elements is not true to position and not true to scale. Unless otherwise stated reference is made to the elucidations concerning the demethanization unit 111' and 112' previously effected in respect of FIG. 3.

In contrast to the low temperature separation illustrated in FIG. 2 in the low temperature separation illustrated in FIG. 3 a material stream formed by combining the material streams u1 and u2 is not yet directly withdrawn in the form of the material stream u but rather said stream, here referred to as u3, is introduced into a second rectification column 212. The liquid, methane-rich stream z is applied at the top of the second rectification column 212 in the form of a reflux.

In this way for a mass flow of for example 3 to 4 t/h the mass flow of ethylene in the material stream u may altogether be reduced to only for example 5 kg/h. The material stream u also contains only for example 6 mol % of oxygen and is therefore to be regarded as non-critical.

To provide the methane-rich reflux onto the second rectification column 212 a compressed methane-rich material stream z0 of for example about 1.5 t/h at a pressure level of for example about 40 bar is provided and in a heat exchanger 213 cooled to a temperature level of for example about −90° C. Decompression in a valve 214 affords a two-phase mixture which is introduced into a separator 215 and phase-separated therein.

In the depicted example the liquid phase is completely introduced into the rectification column 212, the gas phase may in each case be partly or completely introduced into the separating vessels 205, 206, 207 and 208, the rectification column 209 and a separator connected downstream of the tops condenser 211. All of theses introductions are optional and possible alternatives to one another and are therefore illustrated with dashed arrows. They are used in particular for reducing a critical oxygen content in the recited units.

Obtained in the bottom of the second rectification column 212 is a liquid which contains in particular the ethylene recovered using the liquid reflux and is otherwise methane-rich. Said liquid may be introduced in the form of a material stream C into the separator connected downstream of the tops condenser 211 or alternatively, as illustrated with a dashed arrow, recycled directly into the rectification column 209.

The invention claimed is:

1. Process for producing an olefin having N carbon atoms in which using a dehydrogenation a process gas is formed which contains at least the olefin having N carbon atoms, a paraffin having N carbon atoms and a hydrocarbon having N−1 carbon atoms and in which using at least a portion of the process gas a separation input is formed which is subjected to a first low temperature separation in which the separation input is cooled stepwise over a plurality of temperature levels and condensates are separated from the separation input, wherein the condensates are at least partly subjected to a first low temperature rectification to obtain a first gas fraction and a first liquid fraction, wherein the first gas fraction contains at least the olefin having N carbon atoms in a lower proportion than in the condensates and the hydrocarbon having N−1 in a higher proportion than in the condensates, characterized in that the first gas fraction is at least partly subjected to a second low temperature rectification using a liquid reflux containing predominantly or exclusively the hydrocarbon having N−1 carbon atoms in which the first gas fraction undergoes depletion in the olefin having N carbon atoms.

2. Process according to claim 1 in which a proportion of the separation input which remains gaseous in the stepwise cooling is likewise at least partly subjected to the second low temperature rectification.

3. Process according to claim 1 in which in the second low temperature rectification a second gas fraction poor in or free from the olefin having N carbon atoms and a second liquid fraction containing the olefin having N carbon atoms in a higher proportion than in the first gas fraction are formed.

4. Process according to claim 3 in which the second liquid fraction is recycled into the first low temperature rectification.

5. Process according to claim 1 in which the liquid reflux is provided as a liquified gas or in which the liquid reflux is formed using a liquid fraction formed by partial condensation of a gas containing predominantly or exclusively the hydrocarbon having N−1 carbon atoms.

6. Process according to claim 5 in which a proportion which remains gaseous in the partial condensation of the gas containing predominantly or exclusively the hydrocarbon having N−1 carbon atoms is at least partly introduced into the low temperature separation.

7. Process according to claim 5 in which the liquefied gas or the liquefied fraction are partly introduced into the low temperature separation.

8. Process according to claim 1 in which N is two, so that the olefin having N carbon atoms is ethylene, the paraffin having N carbon atoms is ethane and the hydrocarbon having N−1 carbon atoms is methane.

9. Process according to claim 6 in which the dehydrogenation is performed oxidatively.

10. Process according to claim 8 in which the temperature levels to which the separation input is cooled stepwise comprise a first temperature level of −20° C. to −40° C. and/or a second temperature level of −40° C. to −60° C. and/or a third temperature level of −70° C. to −80° C. and/or a fourth temperature level of −95° C. to −105° C.

11. Process according to claim 8 in which the liquid reflux which contains predominantly or exclusively methane is provided in the form of liquefied natural gas or formed using at least a portion of a liquid fraction provided by cooling a predominantly or exclusively methane-containing gas at a pressure level of 30 to 70 bar to a temperature level of −70° C. to −100° C. and decompressing to a pressure level of 10 to 20 bar.

12. Process according to claim 1 in which for the second low temperature rectification a rectification column having 1 to 10 theoretical or practical trays is employed.

13. Process according to claim 1 in which the process gas further contains oxygen and carbon monoxide.

14. Plant (100) for producing an olefin having N carbon atoms, comprising at least one reactor unit (103) adapted for using a dehydrogenation to form a process gas which contains at least the olefin having N carbon atoms, a paraffin having N carbon atoms and a hydrocarbon having N−1 carbon atoms and comprising means adapted for using at least a portion of the process gas to form a separation input and subjecting said input to a first low temperature separation which is adapted for cooling the separation input stepwise over a plurality of temperature levels and separating condensates from the separation input and at least partly subjecting the condensates to a first low temperature rectification to obtain a first gas fraction and a first liquid fraction, wherein the first gas fraction contains at least the olefin having N carbon atoms in a lower proportion than in the condensates and the hydrocarbon having N−1 in a higher proportion than in the condensates, characterized in that means are provided which are adapted for at least partly subjecting the first gas fraction to a second low temperature rectification using a liquid reflux containing predominantly or exclusively the hydrocarbon having N−1 carbon atoms in which the first gas fraction undergoes depletion in the olefin having N carbon atoms.

15. Plant (100) according to claim 14 adapted for performing a process for producing an olefin having N carbon atoms in which using a dehydrogenation a process gas is formed which contains at least the olefin having N carbon atoms, a paraffin having N carbon atoms and a hydrocarbon having N−1 carbon atoms and in which using at least a portion of the process gas a separation input is formed which is subjected to a first low temperature separation in which the separation input is cooled stepwise over a plurality of temperature levels and condensates are separated from the separation input, wherein the condensates are at least partly subjected to a first low temperature rectification to obtain a first gas fraction and a first liquid fraction, wherein the first gas fraction contains at least the olefin having N carbon atoms in a lower proportion than in the condensates and the hydrocarbon having N−1 in a higher proportion than in the condensates, characterized in that the first gas fraction is at least partly subjected to a second low temperature rectification using a liquid reflux containing predominantly or exclusively the hydrocarbon having N−1 carbon atoms in which the first gas fraction undergoes depletion in the olefin having N carbon atoms.

16. Process according to claim 2 in which in the second low temperature rectification a second gas fraction poor in or free from the olefin having N carbon atoms and a second liquid fraction containing the olefin having N carbon atoms in a higher proportion than in the first gas fraction are formed.

17. Process according to claim 2 in which the liquid reflux is provided as a liquified gas or in which the liquid reflux is formed using a liquid fraction formed by partial condensation of a gas containing predominantly or exclusively the hydrocarbon having N−1 carbon atoms.

18. Process according to claim 3 in which the liquid reflux is provided as a liquified gas or in which the liquid reflux is formed using a liquid fraction formed by partial condensation of a gas containing predominantly or exclusively the hydrocarbon having N−1 carbon atoms.

19. Process according to claim 4 in which the liquid reflux is provided as a liquified gas or in which the liquid reflux is formed using a liquid fraction formed by partial condensation of a gas containing predominantly or exclusively the hydrocarbon having N−1 carbon atoms.

20. Process according to claim 6 in which the liquefied gas or the liquefied fraction are partly introduced into the low temperature separation.

* * * * *